United States Patent
King

(10) Patent No.: US 6,217,892 B1
(45) Date of Patent: Apr. 17, 2001

(54) WATER TREATMENT COMPOSITION

(76) Inventor: Joseph A. King, 16261 S. Temple Dr., Minnetonka, MN (US) 55343

( * ) Notice: Subject to any disclaimer, the term of this patent is extended or adjusted under 35 U.S.C. 154(b) by 0 days.

(21) Appl. No.: 08/957,265

(22) Filed: Oct. 24, 1997

(51) Int. Cl.$^7$ ............................................. A01N 25/08
(52) U.S. Cl. ..................... 424/408; 424/405; 424/406; 424/407; 424/421; 424/618
(58) Field of Search .................................... 424/404, 405, 424/406, 408, 417–421, 618, 641, 76.3, 76.8, 78.09, 409

(56) References Cited

U.S. PATENT DOCUMENTS

| | | |
|---|---|---|
| D. 372,760 | 8/1996 | Brancazio et al. ............... D23/209 |
| 1,260,777 | 3/1918 | Kirkegaard . |
| 2,017,456 | 10/1935 | Gudmundsen .................... 210/105 |
| 2,854,038 | 9/1958 | Manley ............................ 141/67 |
| 3,378,027 | 4/1968 | Fredericks et al. ............... 137/268 |
| 3,498,311 | 3/1970 | Hawes, Jr. ....................... 137/101.25 |
| 3,595,394 | 7/1971 | Lorenzen ......................... 210/169 |
| 3,708,122 | 1/1973 | Stuy ................................. 239/317 |
| 3,710,817 | 1/1973 | Lorenzen ......................... 137/268 |
| 3,746,170 | 7/1973 | Bloom et al. .................... 210/198 |
| 3,779,261 | 12/1973 | Zygiel .............................. 137/3 |
| 3,899,425 | 8/1975 | Lewis ............................... 210/206 |
| 3,915,191 | 10/1975 | Eisenthal et al. ................ 137/268 |
| 3,936,364 | 2/1976 | Middle ............................ 426/66 |
| 4,061,435 | 12/1977 | Schmanski et al. ............. 404/10 |
| 4,203,307 | 5/1980 | Obata et al. ..................... 68/17 R |
| 4,249,562 | 2/1981 | King, Sr. .......................... 137/268 |
| 4,265,266 | 5/1981 | Kierbow et al. ................. 137/101.19 |
| 4,270,565 | 6/1981 | King, Sr. .......................... 137/268 |
| 4,331,174 | 5/1982 | King, Sr. .......................... 137/268 |
| 4,364,516 | 12/1982 | Rhoades et al. ................. 239/74 |
| 4,407,865 | 10/1983 | Nice ................................. 427/217 |
| 4,420,394 | 12/1983 | Lewis .............................. 210/169 |
| 4,481,110 | 11/1984 | Shannon ......................... 210/199 |
| 4,504,387 | 3/1985 | LeMire et al. .................. 210/101 |
| 4,608,247 | 8/1986 | Heinig, Jr. ....................... 424/16 |
| 4,610,783 | 9/1986 | Hudson .......................... 210/169 |
| 4,642,192 | 2/1987 | Heskett .......................... 210/638 |
| 4,662,387 | 5/1987 | King, Sr. ......................... 137/268 |
| 4,694,185 | 9/1987 | Weiss ............................. 250/578 |

(List continued on next page.)

FOREIGN PATENT DOCUMENTS

| | | |
|---|---|---|
| 0392443 | * 10/1990 | (EP) . |
| 0429820 | * 5/1991 | (EP) . |
| 0469407 | 2/1992 | (EP) . |
| 0834472 | 4/1998 | (EP) . |

* cited by examiner

Primary Examiner—Neil S. Levy
(74) Attorney, Agent, or Firm—Jacobson & Johnson

(57) ABSTRACT

A regenerative water treatment composition and a process of making a regenerative water treatment composition by retaining a first bacteria killing material such as a zinc in fluid proximity with a second bacteria killing material such as silver chloride for insitu killing of bacteria to allow the silver chloride to continue to kill or damage bacteria that comes into contact with the silver chloride while the zinc carries away the dead bacteria.

7 Claims, 1 Drawing Sheet

U.S. PATENT DOCUMENTS

| | | | | |
|---|---|---|---|---|
| 4,790,981 | 12/1988 | Mayer et al. | | 422/263 |
| 4,858,449 | 8/1989 | Lehn | | 68/12 |
| 4,867,196 | 9/1989 | Zetena et al. | | 137/268 |
| 4,935,116 | 6/1990 | LeMire | | 204/237 |
| 4,964,185 | 10/1990 | Lehn | | 8/158 |
| 5,041,219 | 8/1991 | Strand et al. | | 210/284 |
| 5,053,206 | 10/1991 | Maglio et al. | | 422/264 |
| 5,064,624 | 11/1991 | King | | 422/264 |
| 5,076,315 | 12/1991 | King | | 137/268 |
| 5,124,032 | 6/1992 | Newhard | | 210/169 |
| 5,129,730 | 7/1992 | Someah et al. | | 366/160 |
| 5,149,354 | 9/1992 | Delaney | | 71/67 |
| 5,171,687 | 12/1992 | Moller et al. | | 435/286 |
| 5,201,339 | 4/1993 | Buchan et al. | | 137/268 |
| 5,206,195 | 4/1993 | Ando et al. | * | 502/64 |
| 5,218,983 | 6/1993 | King | | 137/1 |
| 5,234,588 | 8/1993 | Aymes | | 210/202 |
| 5,251,656 | 10/1993 | Sexton, Sr. | | 137/1 |
| 5,350,512 | 9/1994 | Tang | | 210/199 |
| 5,352,369 | 10/1994 | Heinig, Jr. | | 210/760 |
| 5,447,641 | 9/1995 | Wittig | | 210/756 |
| 5,498,333 | 3/1996 | Canther | | 210/198.1 |
| 5,507,945 | 4/1996 | Hansen | | 210/198.1 |
| 5,508,152 | 4/1996 | Toyoda et al. | * | 430/436 |
| 5,614,568 | 3/1997 | Mawatari et al. | * | 523/122 |
| 5,709,870 | 1/1998 | Yoshimura et al. | * | 429/404 |
| 5,869,073 | 2/1999 | Sawan | * | 429/406 |

WATER TREATMENT COMPOSITION

FIELD OF THE INVENTION

This invention relates generally to a coactive bacteria killing composition and to a process of forming a regenerative coactive bacteria killing composition and, more specifically, to a process of forming a water treatment composition having bacteria adhering materials positioned in manner to enable both of the bacteria adhering materials to remain in a bacteria reactive destroying state.

BACKGROUND OF THE INVENTION

In water treatment systems it is believed that a bacteria killing materials such as silver ions are effective in killing bacteria because the bacterial cell walls contain various chemical groups that have an affinity for silver. It is believed that when the bacteria cell wall comes in contact with the silver ion, the bacteria cell is strongly bound to the surface of the silver ion by the various chemical groups in the bacteria cell. The process alone helps prevent the bacteria from multiplying. However, in the presence of dissolved oxygen or very low levels of chlorine a further action can occur in which the various chemical groups in the bacteria cell react chemically with the silver ion and kill the bacteria by damaging or destroying the cell walls of the bacteria. Thus silver ions provide an ideal insitu bacterial killing material, however, without removal of the dead bacteria the surfaces of the silver becomes contaminated with dead bacteria and the reaction stops.

Another bacteria killing material is zinc, the zinc ion is believed to react in a similar manner as the silver ion; however, it is believed that when the zinc ion is present with the silver ion the zinc ion is also effective in keeping the surface of the silver clean so that the silver ions can continue to react or bind with the bacteria in the water.

Although two bacteria killing materials, and particularly two bacteria killing materials such as zinc and a silver containing material such as silver chloride work well together, silver does not have a natural affinity for zinc. Therefor one must be able to retain the silver proximate the zinc so both the zinc and silver can be maintained in a state where they are free to react with the chemicals in the bacteria. The present invention provides a process for forming such a supported relationship between the two materials. The process includes retaining the silver chloride and zinc within a canister so that water can pass through the materials.

In the preferred process it has been found that by use of an adhesive that is securable to both the zinc and the silver can hold the zinc and silver proximate one another. By forming the adhesive in a matrix one can maintain both the silver and the zinc in a reactive state and still provide access to the silver and the zinc so that the bacteria containing water can come into contact with the silver that is dispersed in the matrix. That is, the adhesive, which remains unreactive to the bacteria chemicals, secures the silver therein. By adhesively affixing the silver proximate to the zinc and within an adhesive matrix one provides multiple surfaces areas so the bacteria cells in the water can come into contact with both the silver ions and the zinc ions.

Although an adhesive is described a mechanical restrain of the silver chloride and the zinc would also be suitable as the coaction can be maintained if the zinc and silver containing material are retained in fluid proximity to one another. In the present process the preferred silver containing material is silver chloride.

SUMMARY OF THE INVENTION

Briefly, the present invention comprises a process of adhesively coating a first bacteria killing material such as zinc with a second bacteria killing material such as silver to maintain both the silver and the zinc in a bacteria reactive state by forming an adhesive matrix that is securable to both the zinc and the silver with the matrix providing paths for bacteria laden water to come into contact with both the silver and the zinc to enable the zinc and silver to coactively kill the bacteria in the bacteria laden water and to enable the zinc to remove dead bacteria from the surface of the silver.

DESCRIPTION OF THE PREFERRED EMBODIMENT

In the present process one forms a water treatment composition in pellet form suitable for inserting into an inline feeder in a water supply 14. The water treatment pellets comprise a bacteria adhering carrier, which in the preferred embodiment are zinc pellets. Attached to the zinc pellets is a second bacteria killing material which in the preferred embodiment comprises a silver chloride (AgCl) coating located thereon. The silver chloride particles are suspended in an adhesive matrix that adhesively secures the silver chloride particles proximate to the surface of the zinc pellets to produce a zinc pellet with a silver chloride coating. The matrix allows both the silver and the zinc remain in a reactive state so that both the silver and zinc can be used in a water treatment systems.

Silver chloride is a white powder that can be melted or cast like a metal, and is derived from heating a silver nitrate solution and adding hydrochloric acid or salt solution to the produce a silver chloride solution which is then boiled or filtered in the dark or under a ruby red light to produce the silver chloride powder. In the present process the silver chloride while still in solution is combined with an adhesive to form an adhesive silver chloride solution.

The adhesive and the silver chloride solution are then applied to the zinc pellets. The adhesive is then cured to produce zinc pellets having a silver chloride coating adhesively adhered thereto with both the zinc and the silver chloride available for reacting with the chemicals within a bacteria cell to kill or damage the bacteria. The term adhesively secured herein is meant to include a surface attachment structure between two bacterial adhering materials that does not prevent either of the bacteria adhering materials from binding with the bacteria 15 in the water to damage or destroy the bacteria in the water 14.

Figure 1:
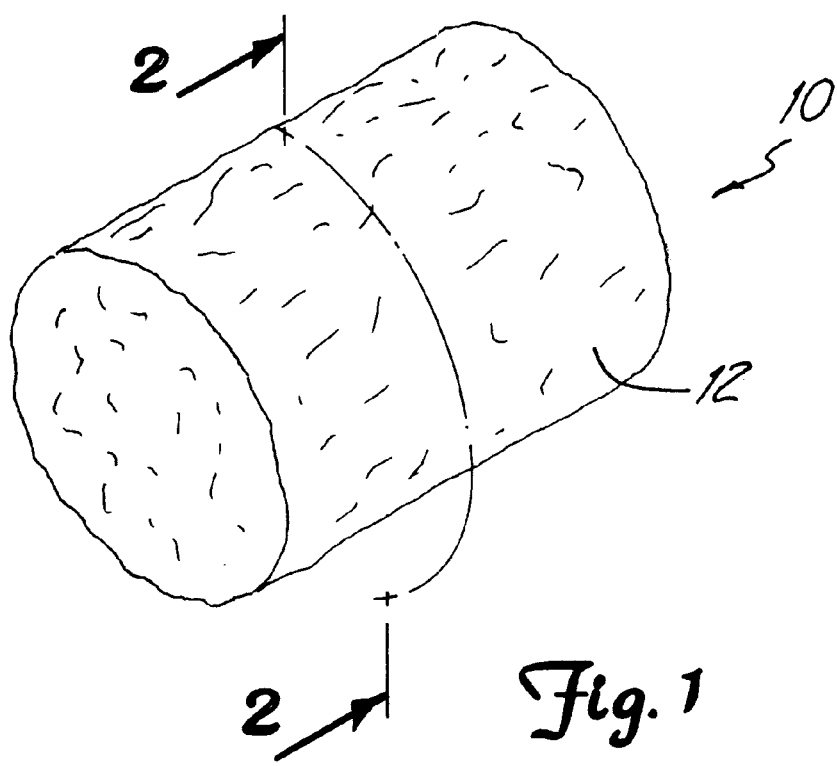
FIG. 1 is a perspective view of zinc pellet having a matrix carrying a silver yielding ion thereon.

Referring to FIG. 1 there is shown a water treatment pellet 10 having an adhesive matrix coating 12. Adhesive matrix coating 12 comprises an adhesive that secures itself to the surface of both the silver chloride 13 and to the zinc pellet 11 without preventing either the zinc or the silver chloride from adhering to and damaging or killing bacteria located in the water. The present process is describe in relation to forming a silver coating on a zinc pellet so that both the zinc and the silver remain in a reactive state to react with the chemicals in the bacteria and effectively damage or kill the bacteria. Thus while the preferred carrier for the silver chloride comprises zinc pellets the carrier need not be zinc as long as the carrier is compatible with the bacteria adhering material on the carrier. The silver chloride coated particle 10 is shown to be in the form of a cylinder and is cut from zinc wire, however, any of many different shape pellets could be used with the present invention.

Figure 2:
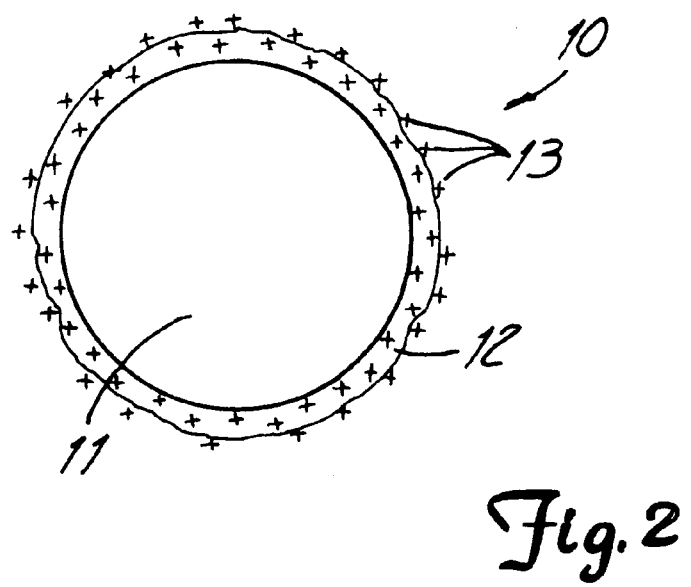
FIG. 2 is a sectional view taken along lines 2—2 of FIG. 1 to show the adhesive matrix located around the zinc pellet.

FIG. 2 is a cross sectional view of the silver chloride coated pellet 10 of FIG. 1 showing zinc particle 11 centrally located within adhesive matrix 12 that contains silver chloride 13 dispersed throughout the adhesive matrix 12. As can be seen from the drawing the silver chloride 13 is maintained in the matrix proximate the zinc pellet 11 to enable water to contact both the zinc and the silver chloride located within the matrix.

In the present invention one coats a particle such as a zinc pellet with a silver ion yielding material such as silver chloride by adhesively affixing or securing the silver chloride and the zinc pellets proximate to each other through a non-soluble water porous adhesive matrix. A suitable material for adhesively securing the silver chloride proximate the zinc pellets is commercially available gelatin which can be cross linked with an aqueous solution of formaldehyde or glutaraldehyde to form a non-soluble water penetrable matrix on the exterior surface of the carrier.

In the present process one forms a plurality of carriers or water treatment members typically an ⅛ inch or smaller which are suitable for inserting into an inline feeder. The zinc pellets which comprise the carrier can be formed from zinc wire by cutting the zinc wire into cylindrical sections about an ⅛ of an inch long.

The following example illustrates how a silver chloride coating was affixed proximate to the exterior surface of a zinc pellet.

EXAMPLE 1

In order to coat a batch of zinc pellets with an adhesive matrix containing silver chloride one mixes 12.5 grams of silver nitrate in 25 ml of distilled water to form an aqueous silver nitrate mixture.

Next one mixes 1.5 grams of gelatin in 25 mil of distilled water to form a gelatin mixture. The gelatin mixture is heated to a temperature of about 140 degrees F.

To eliminate lumps in the gelatin mixture the gelatin mixture is strained through a screen. At this point 5 grams of sodium chloride are mixed into the gelatin mixture. The gelatin mixture was then combined with the aqueous silver nitrate mixture to convert the silver nitrate into silver chloride to thereby form an aqueous silver chloride gelatin mixture. A batch of zinc pellets having a maximum dimension of about ⅛ inch were heated to about 140 degrees F. The pellets are then sprayed with the heated aqueous, silver chloride, gelatin mixture. In order to form a matrix to affix the silver chloride to the zinc pellets the a silver chloride gelatin mixture were immersed in a aqueous bath of glutaraldehyde for about 12 hours to react the gelatin with the glutaraldehyde. The curing produce an adhesive matrix that secured the zinc pellets with the silver chloride that is dispersed throughout the adhesive matrix. After curing the zinc pellets, which are covered with a coating of silver chloride, were rinsed and air dried to produce zinc pellets with a silver chloride coating affixed proximate to the zinc pellets.

EXAMPLE 2

The above process was repeated except instead of immersing the zinc particles with the silver chloride gelatin mixture in an aqueous bath of formaldehyde the zinc particle with the silver chloride gelatin mixture were cured in an aqueous bath of formaldehyde.

In the above examples the zinc pellets had a maximum dimension of about ⅛ of an inch. Larger or smaller pellets could be used; however, for use as a water treatment composition in a dispensing valve it is preferred to have carrier in multiple pellets in order to present a large surface area to the water containing the bacteria.

In the preferred method the adhesive used was gelatin as the gelatin is capable of adhering to the surfaces of both the zinc and the silver chloride. That is, gelatin which can be cross linked in the presence of formaldehyde or glutaraldehyde to obtain the necessary adhesive characteristics remains non-soluble in the water and unreactive with either the zinc or the silver chloride and thus can hold the silver chloride proximate the zinc. That is the cross linked gelatin not only forms a surface attachment but forms a matrix to support or secure the silver chloride in proximity to the surface of the zinc pellet. As the gelatin matrix is securable to the surfaces of both the silver chloride and to the zinc pellets one is assured that the silver and zinc will remain proximate each other so that the regenerative, coactive relationship between the zinc and silver can be retained. While other adhesives could be used gelatin is preferred as it does not leave unwanted residues that might be dissolved in the water during the water treatment process. Also the gelatin is desirable since the porosity of the adhesive matrix formed from gelatin allows bacteria containing water access to both the zinc and the silver to enable the both the zinc and the silver to coactively kill the bacteria in the water.

I claim:

1. A regenerative water treatment method for treating a water supply having bacteria therein, the method comprising;
    providing a carrier with a water-porous, gelatin matrix coating on the carrier, said gelatin matrix adhesively securing a bacteria killing material to the carrier, the bacteria killing material comprising silver chloride; and
    contacting a selected portion of the water supply having bacteria therein with the silver chloride containing, water-porous, gelatin matrix coated carrier to generate silver ions, thereby killing bacteria in the contacted selected portion of water.

2. A regenerative water treatment method according to claim 1 wherein providing a carrier with a water-porous gelatin matrix coating on the carrier includes providing a zinc carrier.

3. A regenerative water treatment method according to claim 1 wherein providing a carrier with a water-porous, gelatin matrix coating on the carrier includes providing a zinc pellet carrier.

4. A regenerative water treatment method according to claim 1 wherein providing a carrier with a water-porous, gelatin matrix coating on the carrier includes providing a nonsoluble surface adhesive to adhesively secure a bacteria killing material to the carrier.

5. A regenerative water treatment method for killing water-carried bacteria in a water supply, the method comprising:
    providing a first bacteria killing material comprising zinc, the zinc generating zinc ions, and a second bacteria killing material comprising silver chloride, the silver chloride generating silver ions, the second bacteria killing material retained in fluid proximity to the first bacteria killing material by an adhesive non-soluble, water-porous, gelatin matrix; and contacting a selected potion of the water supply carrying bacteria therein with both the first bacteria killing material and the second bacteria killing material to enable the zinc ions from the first bacteria killing material and the silver ions from the second bacteria killing material to kill bacteria.

6. A regenerative water treatment method for use in an inline water dispenser comprising;

providing a carrier having an exterior surface, the carrier coated with a non-soluble, water penetrable, gelatin matrix on the exterior surface thereof, the water-penetrable matrix having a bacteria killing material comprising silver chloride dispersed there through;

placing the silver chloride containing gelatin matrix coated carrier in an inline water dispenser; and flowing bacteria containing water through the inline water dispenser, the silver chloride containing gelatin matrix coated carrier generating silver ions so that water flowing past the coated carrier is purged of bacteria by the silver ions, the carrier with bacteria killing material replaceable when said bacteria killing material is spent.

7. A regenerative water treatment method for killing water-carried bacteria in a water supply, the method comprising;

providing a carrier with an exterior surface coated with a water-porous, gelatin matrix, said gelatin matrix adhesively securing a bacteria killing material to the exterior surface of the carrier, the bacteria killing material yielding silver ions in the presence of water for treatment of water to kill bacteria therein; and contacting a selected portion of the water supply having bacteria therein with the bacteria killing material dispersed throughout the water-porous, gelatin matrix coated carrier to generate silver ions in the water, thereby providing for continued killing of bacteria that come in contact with the silver ions in the contacted selected portion of water.

* * * * *